(12) United States Patent
Degert et al.

(10) Patent No.: US 6,844,009 B1
(45) Date of Patent: Jan. 18, 2005

(54) MEDIA IN THE FORM OF COMPLEX DISPERSIONS, METHOD FOR PREPARING SAME AND USES

(75) Inventors: Corinne Degert, Saint Medard en Jalles (FR); Philippe Poulin, Talence (FR); Stéphane Ugazio, Bebington-Wirral (GB); René Laversanne, Pessac (FR); Didier Roux, Merignac (FR)

(73) Assignee: Capsulis, Pessac (FR)

( * ) Notice: Subject to any disclaimer, the term of this patent is extended or adjusted under 35 U.S.C. 154(b) by 0 days.

(21) Appl. No.: 09/936,485

(22) PCT Filed: Mar. 16, 2000

(86) PCT No.: PCT/FR00/00631

§ 371 (c)(1),
(2), (4) Date: Sep. 14, 2001

(87) PCT Pub. No.: WO00/54749

PCT Pub. Date: Sep. 21, 2000

(30) Foreign Application Priority Data

Mar. 16, 1999 (FR) .......................................... 99 03201

(51) Int. Cl.⁷ .............................. A61K 9/16; A61K 9/50
(52) U.S. Cl. ...................... 424/490; 424/400; 424/450; 424/489; 514/937; 514/938
(58) Field of Search ................................ 424/450, 489, 424/490, 400; 514/937, 938

(56) References Cited

U.S. PATENT DOCUMENTS 5,256,422 A * 10/1993 Albert et al. ................ 424/450
6,110,492 A * 8/2000 Alving et al. ............... 424/450

FOREIGN PATENT DOCUMENTS

GB 2079179 * 7/1980
WO WO 98/02144 * 1/1998

* cited by examiner

*Primary Examiner*—Thurman K. Page
*Assistant Examiner*—Charesse Evans
(74) *Attorney, Agent, or Firm*—Dennison, Schultz, Dougherty & MacDonald (57) ABSTRACT

The invention concerns novel media in the form of complex dispersions, method for preparing same and their uses. Said media consist of a first medium in the form of droplets wherein is dispersed a phase containing organized double layers of surfactants, preferably in the form of multilamellar vesicles, said droplets being in emulsion in a second medium called continuous phase non-miscible with the first medium. Said media can be used as base for cosmetic compositions. They can contain active principles, in particular for controlling their release and/or protecting and/or controlling their pH. They can also be used to make polymer microspheres containing an active principle. They are also useful as antigen vector.

49 Claims, 4 Drawing Sheets

♦ FORMULATION A (COMPLEX DISPERSION)
■ FORMULATION B (DOUBLE EMULSION)

FIG.6

△ FORMULATION INITIALLY AT pH=7
■ FORMULATION INITIALLY AT pH=5
♦ FORMULATION INITIALLY AT pH=3.5

MEDIA IN THE FORM OF COMPLEX DISPERSIONS, METHOD FOR PREPARING SAME AND USES

BACKGROUND OF THE INVENTION

The present invention relates to novel media in the form of complex dispersions, to their process of preparation and to their uses.

Various approaches have been used to gradually release active principles by resorting to structured media.

Emulsions are the simplest structured media, with compartments, for example oily compartments, dispersed in an aqueous continuous medium ('direct' or O/W emulsion, the opposite case, water-in-oil, being known as an inverse or $W_1/O$ emulsion). However, these systems, although they are widely used, do not make it possible to separate two media of the same nature, such as a hydrophilic solute which it may be desired to disperse in an aqueous continuous medium while preventing it from dissolving in this continuous medium.

This disadvantage has been circumvented by the use of multiple emulsions consisting of a first emulsion, for example an inverse $W_1/o$ emulsion, of droplets of water in an oily medium, itself emulsified in an aqueous medium $W_2$. A $W_1/O/W_2$ emulsion is thus obtained in which a solute of the internal aqueous medium $W_1$ is theoretically separated from the continuous medium $W_2$ and therefore does not dissolve therein. The opposite case $O_1/W/O_2$ is obviously also possible. For a review of multiple emulsions and their preparation, reference may be made to one of the following documents: S. Matsumoto et al., 'Formation and Application of Multiple Emulsions', J. Dispersion Science and Technology, 10, 455–482 (1989), or C. Prybilsky et al., 'W/O/W Multiple Emulsions: Manufacturing and Formulation Considerations', Cosmetics and Toiletries, 106, 143–150 (1994). Many patents relate to the preparation and in particular the stabilization of multiple emulsions, and to their applications in cosmetics. Mention will be made, in the case of W/O/W emulsions, of: GB 1 541 463 (LION Dentifrice Co.), WO 95/7155 (Beierdsdorf), WO 9422414 (Henkel), FR 9302795 (Roussel-Uclaf) EP 0 731 685 (IFAC), EP 0 692 957 (Goldschmidt), U.S. Pat. No. 5,478, 561 (Lancaster) and EP 92915365 (Emory Univ.). These documents only represent a sample of the many patents in the field, restricted mainly to cosmetics and to pharmaceuticals.

All these documents present conventional processes for the preparation of emulsions, starting from an aqueous phase emulsified in an oil medium using various surfactants. This first emulsion is subsequently itself emulsified in an aqueous continuous medium. The methods for preparing the first emulsion are conventional methods which can be classified into three main methods: mechanical dispersion, phase inversion and spontaneous emulsification. The document EP 92915365 (Emory Univ.) accurately describes these various methods, and gives several general references. In principle, all the methods use, for the emulsification of the water $W_1$ (internal phase) in the oil, a surfactant of low HLB, typically less than 8, generally of nonionic nature. On the other hand, the emulsion of the $W_1/O$ system in $W_2$ uses a surfactant of high HLB which can be nonionic or ionic. Many additives have been described and their use patented in attempting to stabilize these complex systems. The main difficulty arises from the low stability of the $W_1/O$ emulsion and from the tendency of the surfactant used for the second emulsion to destabilize the first. Mention may be made, among the most widely used additives, of sugars (cf. GB 1 541 463) and polymers, intended for example to gel the aqueous phase (cf. FR 9302795). Moreover, several examples are found in the literature of the use of polymer surfactants which clearly stabilize multiple emulsions (cf., for example, GB 1 541 463, which uses Pluronic®, U.S. Pat. No. 5,478,561, which uses polyglycerol esters, or WO 9422414, which uses polyalkylene derivatives).

Many documents are found in the literature which describe media in which an active principle is found encapsulated within vesicles, known as lamellar vesicles, comprising at least one bilayer of surfactants. These vesicles are often denoted by unilamellar, paucilamellar or multilamellar vesicles, according to whether they comprise one, a limited number or a large number of bilayers. Liposomes and niosomes® are examples of surfactant-based lamellar vesicles.

Multilamellar vesicles include those, hereinafter denoted by vesicles with an onion structure, which are vesicles with an essentially spherical shape composed of a uniform sequence of concentric bilayers, from the –20 center to the periphery of the vesicles.

Such vesicles are clearly distinguished from conventional multilamellar liposomes by the uniformity of the stacking of the surfactant bilayers from which they are formed. The uniformity of this stacking results from the thermodynamic nature of the vesicles and from their liquid crystal symmetry.

These structures can be demonstrated by microscopic examination of the compositions. Observation is carried out using a polarized-light optical microscope, in which a birefringent lamellar phase is visible. It is expressed by a characteristic texture, related to the presence of defects (grain boundaries) between phase domains oriented in different directions. In the case of the concentrated vesicle phase, the texture is characterized by its uniform and fine nature, related to the size of the vesicles. In the dispersed vesicle phase, the vesicles are visible in the form of slightly birefringent points which are more or less resolved (according to the size). Birefringence is only observed when the dispersion is not too dilute or when the vesicles are sufficiently large (typically with a diameter of greater than 5 $\mu$m). Therefore, if the dispersion is relatively dilute, there will be grounds for carrying out a preliminary concentrating operation in order to clearly demonstrate the birefringence characteristic of the presence of these vesicles.

Such vesicles can be obtained by conversion of a lamellar liquid crystal phase incorporating at least one surfactant under the effect of shearing. Examples of the preparation and use of such multilamellar vesicles are given in particular in International Applications WO 93/19735, WO 95/18601, WO 95/19707, WO 97/00623 and WO 98/02144.

Multilamellar vesicles comprising surfactants, in particular vesicles with an onion structure, are systems which can encapsulate or incorporate active principles, creating an internal medium, different from the external medium, within which the active principles are retained. The retention of the active principle inside the vesicle has two causes:

Thermodynamic: the difference in affinity of the active principle between the external medium and the internal medium results in its partition between the two media. For this reason, in the example of an aqueous dispersion of the vesicles, an amphiphilic active principle will be preferentially localized within the vesicles, whereas a very hydrophilic active principle will be localized instead in the external medium and will thus be only very weakly encapsulated.

Kinetic: each surfactant-based membrane forms a diffusion barrier which slows down the passage and thus the escape of the active principle toward the outside. This mechanism is all the more effective as the active principle is a large molecule, the diffusion coefficient of which will be low.

It will thus be noted, quite obviously, that a small and very hydrophilic molecule will not be, or will only be very slightly, encapsulated in the vesicles, since its affinity will give it a preference for the external medium (still assuming a dispersion of the vesicles in an aqueous medium) and since the barriers formed by the surfactant bilayers will only be slightly effective in retaining it. A small or large molecule is understood to mean a molecule with a molar mass respectively of less than 500 or greater than 1000 g/mol. The same reasoning holds for the encapsulation of a very lipophilic molecule when the vesicles are dispersed in an oily medium.

In the same way, and to an even more marked extent, the same mechanisms are involved during the encapsulation of molecules in conventional liposomes, which are vesicles formed from a small number of bilayers throughout an aqueous core (or several) aqueous cores.

In this case, first, the medium of the aqueous core is very similar to the external medium and thus the difference in affinity of the encapsulated active principle will be very low, and, secondly, the low number of membranes implies an overall diffusion barrier which is much less effective.

There is also a technical need to improve encapsulation systems based on surfactant membranes in order, in particular, to confer better leaktightness thereon. In fact, there is little scope for possible adjustment with respect to the thermodynamic parameter, apart from the specific choice of surfactants. However, when a product is soluble in water, the modification of the surfactant may make virtually no improvement to its coefficient of partition between the water of the external phase and the interior of the vesicle. Furthermore, the external medium is often a complex medium itself comprising surfactants (the case of emulsions or shampoos) or other components (polymers, electrolytes, and the like) capable of increasing the affinity of the active principle for this medium and thus of further disadvantaging its coefficient of partition with the outside.

The only effective means a priori is thus to vary the kinetics of escape. To do this, the leaktightness of the barriers can be modified, for example by changing surfactants, or this leaktightness can be reinforced by incorporation of a polymer in the membranes or in the aqueous layers. This method encounters difficulties of a practical nature (the surfactants which can be used to form the membranes all have fairly similar diffusion properties) but also theoretical difficulties: the introduction of a polymer into a layer with a thickness of a few manometers introduces, in many cases, only a relatively ineffective diffusion barrier, the polymer layer being virtually monomolecular.

Another method consists in coating the vesicle in a 'shell' of polymer via a conventional method of encapsulation by polymer, such as, for example, coacervation. This method, while attractive, exhibits several difficulties, first with regard to its implementation and secondly with regard to the characteristics of the objects obtained. Vesicles made of surfactant membranes generally have sizes in the region of a micrometer, whereas capsules obtained by coacervation have diameters of between several tens of and several hundred micrometers. Furthermore, coacervation is usually carried out using an emulsion, the polymer or polymers during their 'insolubilization' being adsorbed at the interface between the oil and the water around each droplet of the emulsion. It is not certain that the adsorption of the polymer is possible or at least effective at the interface between the water and the external surfactant layer of the vesicles. Coacervation techniques are thus not entirely suited to the coating of surfactant-based vesicles. Furthermore, the objects obtained by this technique are microcapsules which have to be ruptured to release the active principle, in contrast to vesicles, which release their active principle slowly by diffusion. To coat the vesicles with a polymer shell will thus profoundly change the nature of the vesicles and in particular their destination and their use. It is the same for other techniques for coating by polymer, such as atomization.

SUMMARY OF THE INVENTION

The inventors of the present invention have now discovered that it is possible to prepare dispersed media not exhibiting the disadvantages of those of the prior art described above by using surfactant-based multilamellar vesicles as internal medium and by dispersing them in a hydrophobic phase which is subsequently emulsified in an aqueous phase.

The inventors have subsequently been able to extend the same concept to the aqueous media obtained by emulsification in a hydrophobic medium of an aqueous medium comprising a dispersion of surfactant-based vesicles.

It is well known that surfactants, which are amphiphilic compounds, have the ability to self associate in the form of membranes, which can either form objects closed onto themselves, which are vesicles, or, at a higher concentration, be organized in the form of a lyotropic structure having a liquid crystal organization.

The inventors of the present invention subsequently noticed that the same advantages can be obtained by replacing the initial phase of vesicles with any phase comprising surfactant membranes in an organized state.

Such phases comprising membranes in an organized state can in particular be any phase of lyotropic phase type capable of being dispersed in a medium.

The term 'lyotropic phase' is understood to mean any organized phase having a liquid crystal symmetry formed from at least one surfactant and from a medium which is either polar, for example aqueous, or nonpolar, for example oily. Lyotropic phases are not solely lamellar (also known as smectic A phases) but can have other structures with different symmetries: hexagonal, cubic, and the like.

Lyotropic phases are condensed phases of surfactant membranes, generally concentrated in surfactants, at thermodynamic equilibrium, the membranes being separated from one another by a medium of different polarity. If the medium is more polar than the surfactant membrane (for example water), a direct phase is present; in the opposite case (for example, oil), an inverse phase is present. (A description and schemes of these phases can be found in C. L. Khetrapol, A. C. Kunwar, A. S. Tracy, P. Diels, in Nuclear magnetic resonance studies in lyotropic liquid-crystals, 1975.)

The lamellar phases are examples thereof which are simple to visualize, in which the membranes, which are flat overall, are simply stacked on one another and separated by layers of polar medium or of oil. In the hexagonal phases, the surfactants form tubes arranged in space according to a hexagonal arrangement. All these phases are anisotropic and exhibit a liquid crystal order. Cubic phases also exist. Furthermore, these phases exhibit orientation defects and are generally composed of a multitude of 'grains' separated by lines of defects (grain boundaries) which are so many regions of weakness which allow them to be dispersed (like a powder for a crystal).

DETAILED DESCRIPTION OF THE INVENTION

According to a first aspect of the invention, a novel medium is now provided which is prepared from a phase comprising bilayers of surfactants in an organized state, which phase is subsequently dispersed in a first medium. It is this medium comprising this dispersion of bilayers which is subsequently emulsified in a second medium immiscible with the first.

This novel medium and its method of preparation differ greatly from the multiple emulsions of the prior art essentially in so far as the starting material, according to the present invention, is not an emulsion but a dispersion of already preformed objects, which in particular avoids recourse to significant shearing, as is necessary in the case of a multiple emulsion for preparing the first emulsion.

Such a medium differs fundamentally from a multiple emulsion because, in the case of this medium, the internal phase is formed and structured prior to the dispersion stage, whereas, in the case of a multiple emulsion, the starting material is an aqueous phase which is conventionally emulsified in the oily medium. This difference has not insignificant consequences because this preliminary preparation confers much better stability on the internal phase, related to the intrinsic stability of this preexisting phase.

Another advantage is that, in the case of vesicles, the size of the dispersed objects is fixed prior to the dispersion stage.

Another advantage in the case of the media of the present invention is that, at least in the case of lyotropic media and multilamellar vesicles with an onion structure, the dispersed objects are objects having an internal structure resulting from a thermodynamic equilibrium.

Another advantage of the objects dispersed in the media of the present invention is that they are not a priori capable of undergoing phenomena of coalescence and Ostwald aging, which are major causes of the destabilization of multiple emulsions.

Another advantage of the media of the invention is that they exhibit the organoleptic characteristics (feel, consistency, and the like) of multiple emulsions and consequently constitute systems which are particularly advantageous for the cosmetic or dermatological industry, where they can be used as vehicles for both hydrophilic and lipophilic active principles and also as bases for cosmetic or dermatological products with a topical action.

Furthermore, the presence in the complex media of the invention of the phase comprising bilayers confers additional advantages on the medium of the invention. This is because it is possible to improve the protection and/or to control the release of an active principle, in particular of a chemical or biological active principle, by incorporating this active principle within the phase comprising the bilayers.

Another particularly advantageous use consists in using the media of the invention as true microreactors, making it possible to temporarily isolate certain reactants and/or to control their pH.

Another use of the complex media of the invention is that it is possible to use them as antigen vectors, resulting in an amplified immune response.

This is because modern vaccination, in particular that using antigen subunits, such as recombinant proteins, glycoproteins, peptides or polysaccharides, is based on the induction of an immune response by the administration of the antigen by various routes.

However, this response is generally insufficient to introduce vaccinal protection when the antigen is administered directly. The induction of effective protection requires the use of adjuvants or of vectors capable of sufficiently amplifying the response of the immune system to the antigen administered. Many systems have been developed to meet this requirement. Some examples can be found, for example, in Allison A. C., Arch. Immunol. Ther. Exp., 1997, 45, p. 141–7, O'Hagan D. T., J. Pharma. Pharmacol., 1998, 50 p.1–10 or Bennett B. et al., J. Immunol. Methods, 1992, 153, p. 31–40. Several of the examples mentioned in these articles reveal the effectiveness of the use of an emulsion of the antigen in an oil in order to act as adjuvant for this antigen.

European patent EP 0 480 981 also discloses multiple emulsions of W/O/W type which can be used as vaccines.

The inventors have now observed that the media of the invention are notable antigen vectors. More specifically, it transpires that an antigen can be incorporated in a phase comprising bilayers of surfactants in an organized state, preferably in multilamellar vesicles, preferably in multilamellar vesicles with an onion structure, and that it is subsequently possible, by dispersion of this phase comprising bilayers in an organized state in an oil and then emulsification of this oil in an appropriate buffer, to obtain a particularly immunogenic preparation which induces a much stronger immune response than the antigen alone or than the antigen simply incorporated within said phase comprising surfactant-based bilayers.

Finally, another application consists in using these media to prepare microspheres composed of polymers comprising an active principle.

Thus, according to a second aspect, the invention includes various applications of the complex media of the invention related to the advantages listed above.

Other advantages justifying the applications of the media of the present invention will become more clearly apparent in the light of the description and examples which follow.

According to one of its essential characteristics, the invention relates to a complex medium composed of a first medium in the form of droplets, in which droplets is dispersed a phase comprising organized bilayers of surfactants, said droplets being in emulsion within a second medium, known as the continuous phase, which is immiscible with the first medium.

The sizes of the droplets of the first medium are advantageously between 1 and 100 $\mu$m, preferably between 1 and 50 $\mu$m.

The emulsion advantageously comprises from 1 to 90% by mass of medium dispersed in the continuous medium, preferably from 1 to 60%.

The bilayers, in the organized form, advantageously represent, by mass, from 1 to 90%, preferably from 25 to 75%, with respect to the droplets.

The first medium can be an aqueous medium and the continuous phase will then be a hydrophobic medium.

However, according to a preferred alternative form of the invention, the first medium is a hydrophobic medium and the continuous phase is an aqueous medium.

Use will be made, as hydrophobic medium, of, for example, a mineral or vegetable oil, a silicone oil or an organic solvent which is immiscible with water.

The phrase 'phase comprising organized bilayers' is understood to mean both lyotropic systems and lamellar vesicles.

Any lyotropic phase, from the moment when it is dispersible in a medium, can be used to form complex dispersions according to the invention.

The preferred media of the invention comprise multilamellar vesicles dispersed within a medium itself emulsified in a continuous phase which is immiscible with this first media.

The preferred media according to the invention comprise a dispersion of multilamellar vesicles with an onion structure, the vesicles being as defined above.

The size of the multilamellar vesicles is advantageously between 0.1 and 20 μm, preferably between 0.1 and 10 μm.

The proportions of vesicles in the droplets, advantageously in oil droplets, are preferably between 1 and 90% by mass, typically between 25 and 75%.

For reasons of simplicity, the more detailed description which will follow will be made in the case of vesicles with an onion structure dispersed in a hydrophobic medium, itself emulsified in an aqueous medium.

However, a person skilled in the art can easily generalize the information given in the present document by extending it to inverse systems in which vesicles are dispersed in an aqueous medium and then this dispersion is emulsified in a hydrophobic medium. A person skilled in the art will not experience the least difficulty either in generalizing the teaching of this document to the case of organized phases of bilayers, whether direct dispersions or inverse dispersions.

Thus, the teaching of this document will be easily generalized to inverse systems in which the hydrophobic objects are dispersed in an aqueous medium and this dispersion is used in an emulsion of water-in-oil type.

This is because a person skilled in the art knows that lyotropic phases exist in which surfactant membranes are separated by oil layers.

Such phases can be dispersed in an aqueous medium to give an aqueous dispersion of small 'grains' of lyotropic phases. This aqueous medium can subsequently be used to prepare an emulsion of water-in-oil type. The equivalent of an O/W/O multiple emulsion is thus obtained. Examples of multiple emulsions of O/W/O type are given in Patent Applications EP 0 836 847, EP 0 782 646 or EP 0 559 013 and in French Application FR 96.10140 which uses fluorinated oils.

A person skilled in the art knows how to prepare vesicles, in particular vesicles with a multilamellar onion structure, while using formulations which render them dispersible in a hydrophobic medium. Such vesicles are disclosed in particular in International Application WO 95/18601 on page 4, line 32, and in Examples 11 and 12 of this same application.

It is subsequently possible to use the oil in which the vesicles have been dispersed beforehand to form an emulsion in an aqueous continuous medium.

A person skilled in the art will have no difficulty in choosing the surfactant used to create the external O/W emulsion, so as to avoid destabilizing the multilamellar arrangement of the vesicles and destructuring them, while taking into account in particular that the high concentration of surfactant in the vesicles, if a surfactant is not carefully chosen, is capable of destabilizing the external emulsion over short periods of time. Furthermore, the choice of the oil is not irrelevant, as the dispersibility of the vesicles varies greatly according to whether a vegetable, mineral or silicone oil is chosen. Generally, the choice of the oil will be determined by the type of application envisaged. It will thus be necessary to adapt the surfactant system to the type of oil used.

A person skilled in the art will easily understand that, by correctly choosing the system of surfactants used to create the vesicles, the surfactant used to form the exterior emulsion and the oil of the intermediate phase, it is possible to confer excellent stability and a good capacity to retain a water-soluble active principle without diffusion from the internal medium (vesicles) toward the external aqueous continuous medium.

Thus, according to an advantageous alternative form, polymer surfactants are used to form the vesicle and/or to emulsify the oil comprising the dispersion of vesicles in water. The surfactants of polymer type are preferably chosen from a family in which can be found compounds of different HLB, so as to be able to use a compound of 'low' HLB for the preparation of vesicles, which will thus be dispersible in an oil, and a compound resulting from the same family but of 'high' HLB for the preparation of the external O/W emulsion. It is clear to a person skilled in the art that the notion of 'low' and 'high' HLB is difficult to give a very precise figure to. However, it is known that surfactants of low HLB are more easily dispersible in the oil. The term 'low HLB' can be understood to mean an HLB of less than 8 but there is no clear-cut limit. In particular, phospholipids do not have a very clear HLB value and are dispersible in an oily medium and in an aqueous medium. However, it is entirely possible to envisage having a polymer surfactant of low HLB of a given family for the preparation of the vesicles and a surfactant of high HLB of another family for the aqueous emulsification of the oily dispersion of vesicles. Several main families come up to this expectation:

Poloxamers, which are di- or triblock polymers of ethylene oxide and of propylene oxide, the ratio between the lengths of each block fixing the HLB (polypropylene oxide (also known as polypropylene glycol) acting as lipophilic part, whereas the part based on ethylene oxide is hydrophilic). These compounds are represented in particular in the family of Pluronic® and Lutrol® products from BASF.

Copolymers of polyalkylene glycol and of alkyl glycol. The length of the PEG part and the possible methoxylation of the end hydroxyl groups makes it possible to modify the HLB of the compound within a wide range. Thus, a methoxy PEG-17 dodecyl glycol copolymer will have an HLB of 21 and will thus be suitable for the emulsification of the oily dispersion of vesicles in water, whereas a copolymer of PEG-45 and of dodecyl glycol will have an HLB of 4.4 and will thus be suitable for the formulation of the vesicles dispersible in the oil. These compounds are sold, for example, by Akzo Nobel under the Elfacos® range.

Polyglycerides, which are esters of fatty acids and of glycerol polymers. By varying the chain length of the fatty acid, the number of substituent chains and the degree of polymerization of the glycerol, the HLB can be varied within a wide range, Ethers of fatty alcohols and of glycerol polymers, in which the ester functional group of the polyglycerides has been replaced by an ether functional group, which are more resistant to hydrolysis, Esters of fatty acids and of polyethylene glycol, also known as polyoxyl n stearate, in the case of an ester of stearic acid, where n is the mean length of the polyethylene glycol chain. The polyethylene glycol chain can be esterified at just one or both ends.

Ethers of fatty alcohols and of polyethylene glycol, also known as polyoxyl n alkyl ethers, where n represents the mean number of ethylene oxide units in the chain.

Mixtures of esters of glycerol and of esters of polyethylene glycol. By varying the chain length of the fatty acid, the number of chains and their substitution, the HLB can be varied. These products are sold, for example, by Gattefosse (Lyons, France) under the names Gelucire® or Labrafil®.

Polyoxyethylenated hydrogenated castor oil (ethoxylated glycerol ester), resulting from the reaction of hydrogenated castor oil with ethylene oxide. The HLB is adjusted by the number of ethylene oxide groups.

Polyoxyethylenated castor oil (ethoxylated glycerol ricinoleate).

Polymethylcyclosiloxane, for example the products from the cyclomethicone and dimethicone copolyol families, such as the products from Dow Corning (DC3225C and DC 5200).

These families are given as examples and do not constitute an exhaustive list. The notion of polymer is taken here in the broadest sense of a molecule with a high molar mass, it being possible for some of the compounds to be regarded as oligomers, others not being polymers in the strict sense of a molecule formed from a repetition of identical units. It is difficult to define a minimum molecular mass in speaking of polymer. A limit may be set of a molar mass of greater than 1000 Da, which is a value beyond which diffusion begins to be quite low.

At least one of the surfactants is advantageously of polymer type but it is in no way essential for polymer surfactants to be used, both in the vesicles and in the external emulsion. The use of polymer surfactants in the two compartments certainly reinforces the stability and in particular the leaktightness of the combined unit but, in the case where the solute to be encapsulated inside the vesicles is not too small, vesicles formed from non-polymer surfactants may be sufficient to produce a stable emulsion of droplets of oil in water, inside which droplets are dispersed the vesicles encapsulating the active principle. In this case, the vesicles can be obtained from any surfactant with an HLB low enough to allow them to be dispersed in the oil. This is a case with phospholipids or sugar esters of low HLB.

As set out above, the media of the invention can comprise one or more active principles in one or other of the media constituting the complex media of the invention. They can in particular comprise one or more active principles enclosed within the phase comprising the bilayers, with the advantages presented in the following of the account and related to the various applications set out below.

The preparation of the media of the invention generally comprises three stages:

the preparation of a phase comprising bilayers of surfactants in an organized state, the dispersion of this phase in a first medium, the emulsification of the dispersion thus obtained in a second medium, immiscible with the first medium, by means of a surfactant, preferably a surfactant of polymer type.

One or more active principles can be incorporated, both in the phase comprising the bilayers and in the first or the second medium.

They can in particular be chemical or biological active principles.

In the specific case of the preferred media of the invention composed of dispersions of multilamellar vesicles, preferably of multilamellar vesicles with an onion structure, in a hydrophobic medium which is emulsified in an aqueous continuous medium, the following three steps will preferably be carried out:

Preparation of surfactant-based vesicles, for example by the method disclosed in one of the abovementioned patents, by homogeneous or nonhomogeneous shearing of a lyotropic lamellar phase, but also by any other literature method resulting in vesicles, for example lipid vesicles. The use of multilamellar vesicles, by their better stability and their better leaktightness, related to the largest number of membranes composing them, may be preferred in the case where these characteristics would be important for the final product.

Dispersion of these vesicles in a hydrophobic medium, for example a mineral, vegetable or silicone oil, it being possible for the hydrophobic phase optionally to comprise a lipophilic active principle or additive, for example an antioxidant or a preservative.

One or more thickening additives can also be added to the oil, if it is not desired to use directly an excessively viscous oil. The oil can be chosen according to its characteristics of dissolving the active principle (an oil will be chosen in which the active principle is the least soluble, in order to improve the leaktightness) but also according to its viscosity (a high viscosity will reduce the diffusion of the active principle).

Emulsification of this dispersion of vesicles in the oil in an aqueous continuous phase by means of a surfactant, preferably a polymer surfactant. The external medium can be water, an aqueous solution or a medium which is itself complex, such as a shampoo or a gel for example.

The vesicles are advantageously formulated with surfactants of low HLB, preferably, whether they are or are not polymers, so that their dispersion in the oil is spontaneous or obtained by simple stirring. This is a big difference from conventional methods for the preparation of multiple emulsions, in which the first step is an emulsification step, all the technical difficulties in the implementation of which, in particular in the case of inverse emulsions, are known to a person skilled in the art. It is important to note that the absence of this initial step of emulsification of an aqueous phase in the oil frees the process from the need sometimes encountered to subject the system to high shearing or to relatively high temperatures, which is very important in the case of the encapsulation of sensitive molecules, for example biological molecules.

Another big difference from conventional multiple emulsion systems is the presence of the vesicle, which acts as a reservoir of the active principle by encapsulating it, which will give much greater leaktightness to this type of system, limiting the possibilities of migration of the active principle between the internal aqueous phase and the external aqueous continuous phase. Furthermore, coupling of the two technologies, of encapsulation by surfactant vesicles and of emulsions, makes it possible to obtain a synergy of the advantages of these two methods. In the same way, a cosmetic or therapeutic active principle of a topical preparation can be protected, for example from oxidation, during its storage (effect of the emulsion) and can be made available during the application in a form which promotes its cutaneous penetration (effect of the vesicles).

One of the main advantages of the invention is that of being able to result in an encapsulation system which is much more leaktight than those of the usual techniques using surfactant-based vesicles or than those of multiple emulsion techniques, without having the disadvantages of the techniques of coating by polymers (difficult and expensive to implement, large capsules which give an unpleasant texture, need to rupture the polymer shell in order to release the active principle, and the like).

According to another aspect, the invention also relates to the use of the media of the invention.

These media, as indicated above, can be used in particular in the field of cosmetics or dermatology. This is because the cosmetics industry is constantly looking for novel media with a pleasant consistency and texture in order to create novel bases for products for caring for the skin. Multiple emulsions, for example, are very particularly sought after by the cosmetics industry as cream base for their particularly pleasant feel. However, they suffer from their lack of stability and from their difficulty of preparation, due to the sensitivity of the first emulsion to the process for the manufacture of the second emulsion. The complex media of the present invention prove to be particularly advantageous in this application as they exhibit the organoleptic advantages (feel, consistency and the like) of multiple emulsions without having the disadvantages thereof. They thus constitute particularly advantageous systems for the cosmetics industry as they are, independently of their ability to incorporate an active principle within the phase comprising the bilayers.

Other uses, for their part more particularly related to the advantages obtained as a result of the incorporation of an active principle within the phase comprising the bilayers, are set out below.

Thus, as a result of the kinetic and not thermodynamic control of the escape, the invention will be particularly advantageous in all cases where it is desired to isolate an active principle which is soluble in water but of low molar mass (thus with a high coefficient of diffusion in surfactant membranes) from an aqueous continuous medium. It is particularly useful for the case where it would be desired to protect said active principle from decomposition, for example decomposition related to hydrolysis or to oxidation.

There are many examples of such active principles and mention may be made, as non exhaustive examples, of:

water-soluble vitamins hydroxyketones, such as dihydroxyaketone and erythrulose

α-hydroxy acids (glycolic acid, lactic acid, and the like)

electrolytes plant or marine aqueous or aqueous/glycolic extracts procyanidol oligomers, and other polyphenol derivatives.

Furthermore, the method can be used to protect a water-soluble active principle of a small or large molar mass from the action of small solutes present in the −20 external medium which, without this, would migrate very rapidly from the dispersion medium toward the inside of the vesicles and might destroy or modify the active principle.

A particularly advantageous application is the case where the active principle has to be maintained at a given pH, whereas the finished product, for example for reasons of safety, has to be formulated at a different pH. This is a case with α-hydroxy acids, which, to be active, have to remain at a pH below 3 but which are introduced into cosmetic preparations for which the pH has to be in the region of 7. This is also the case with potassium thioglycolate, used in depilatory creams, which is active at a pH of greater than 9 but which is preferably present in creams with a pH in the region of 7. By creating a kinetic barrier between external medium and internal medium, the invention makes it possible to achieve such a performance.

More generally, the invention makes it possible to have available true microreactors in which a reactant is incorporated in one compartment of the system and the other reactant of a desired reaction in enclosed in the other compartment. The reaction can take place either by triggering, by virtue of rupturing the external emulsion (under the effect of a modification in temperature or by addition of a suitable additive, for example), or, on the contrary, very slowly by diffusion of the reactants, it being possible for this diffusion to be adjusted by the choice of the surfactants and the intermediate oil.

The complex media according to the invention can also be used as antigen vector in order to induce a sufficiently strong immune response. To this end, the antigen will be enclosed within the phase comprising the organized bilayers.

According to a particularly advantageous alternative form, the antigen will be enclosed within multilamellar vesicles, preferably with an onion structure, themselves dispersed in droplets of oil emulsified in water. The inclusion of the antigen in such a medium makes it possible simultaneously to vectorize the antigen, to protect it from external attacks, in particular from being destroyed by the enzymes present in the body, and to make it available to the immune system. In comparison with conventional emulsions used as antigen adjuvant, of water-in-oil type, the invention is provided in the form of an oil-in-water emulsion, which is much more stable and easier to inject or to administer.

According to another particularly advantageous alternative form of the invention, the first medium is a hydrophobic medium comprising a substance capable of solidifying, of thickening, of polymerizing or of precipitating or a solution of such a substance in a water-immiscible solvent capable of evaporating. The advantage of such a medium is that of reinforcing the leaktightness of the hydrophobic phase and the robustness of the system obtained after emulsification.

Mention will be made, as substance capable of solidifying or of thickening, of waxes and polymers with a melting or fluidification point such that it is possible to form the system comprising the bilayers within the liquid phase of the substance and then, by lowering the temperature, to obtain a system where the hydrophobic medium is solidified or sufficiently thickened to slow down the diffusion phenomena.

It is also possible to dissolve a monomer in the hydrophobic medium or a polymer capable of being crosslinked and to bring about, after the formation of the complex dispersion, the polymerization of the monomer or the crosslinking of the polymer by a chemical, thermal, photochemical or radiochemical method. In this case, the droplet of dispersion of phase comprising bilayers will have been replaced by a sphere formed from a polymer matrix incorporating grains of this phase, which is much more stable.

In the same way, it is possible to use, as hydrophobic medium for dispersing the phase comprising the bilayers, a solution of a polymer in a volatile hydrophobic solvent. After formation of the complex dispersion, the evaporation of the solvent results in precipitation of the polymer in the form of hard spheres which trap the grains of phase comprising bilayers.

The invention is thus also a novel method of preparation of microspheres which are provided as polymer matrices incorporating an active principle, in this case in the form of (or enclosed within) grains of phase comprising bilayers, in particular of lyotropic phase.

Such a process comprises:

the preparation of a phase comprising bilayers of surfactants in an organized state, including said active principle, the dispersion of this phase in a hydrophobic medium in which a monomer or a polymer capable of being crosslinked is dissolved or in a medium composed of a hydrophobic solvent in which a polymer is dissolved, the preparation of an emulsion in the form of droplets of said dispersion in a medium which is immiscible with the above hydrophobic medium, the conversion of said droplets into solid grains, respectively by polymerization of the monomer or crosslinking of the polymer or precipitation of the polymer.

Such an alternative form is very particularly advantageous in the case of multilamellar vesicles, in particular in the case of multilamellar vesicles with an onion structure.

This particularly advantageous alternative form of the invention makes possible the preparation of polymer microspheres in which active principles can be encapsulated, in particular pharmaceutical active principles, such as, for example, peptides, proteins (including enzymes) or any molecule which can benefit from such an encapsulation (delay effect, protection of the molecule and the like). In this case, the polymer can advantageously be chosen from resorbable polymers usable in parenteral injection, such as PlaGa (polylactide glucoside).

The invention thus provides, according to this final alternative form, a means for incorporating, in a medium, a wide range of active principles which can be either water-soluble or lipo-soluble. However, it applies essentially to water-soluble active principles.

The examples which follow illustrate the present invention in a non limiting way.

More specifically,

Example 1 gives a formulation example and illustrates the preparation of a complex medium according to the invention composed of an emulsion in an aqueous continuous medium of droplets of mineral oil, in which droplets vesicles with an onion structure including vitamin C are dispersed, Example 2 demonstrates, by polarized-light and direct-light optical micrococscopy, the structure of the complex media of the invention, in comparison with media in the form of a double emulsion, Example 3 describes a kinetic study on the escape of an active principle and demonstrates the advantage of the media of the invention in isolating an active principle from the external medium, Example 4 demonstrates the difference in stability between a double emulsion and a complex dispersion according to the invention, Example 5 demonstrates the use of the media of the invention in preparing complex media exhibiting pH differentials between different compartments, Example 6 illustrates one use of the complex media according to the invention in creating a pH differential, Example 7 shows the advantage of the media of the invention in the preparation of a cosmetic emulsion comprising a particularly unstable active principle, Example 8 illustrates the use of the complex media of the invention in preparing microspheres composed of a resorbable polymer, Example 9 illustrates the use of the complex media of the invention as antigen vector which makes it possible to obtain a marked amplification of the immune response.

BRIEF DESCRIPTION OF THE DRAWINGS

FIGS. 1 to 8 are given with reference to the examples. More specifically:

FIGS. 1 to 4, corresponding to Example 2, represent negatives obtained in direct-light optical microscopy (FIG. 1 and FIG. 2) or in polarized-light microscopy (FIG. 3 and FIG. 4), with a 20× objective and a 10× eyepiece. More specifically:

FIG. 4 represents the negative obtained in polarized light in the case of the complex medium according to the invention obtained in example 2, FIG. 5 given with reference to example 3, gives the kinetics of escape of vitamin C and represents, more specifically on the ordinate, the percentage of vitamin C which remains encapsulated as a function of the time shown in days on the abscissa, FIG. 6, given with reference to example 5, gives the change as a function of the time of the encapsulation yield in the formulations A and B described in this example, FIG. 7 given with reference to example 6, gives the change as a function of the time of the pH of three different formulations according to the invention.

EXAMPLES

Example 1

Formulation Example

The implementation of the process according to the invention takes place in several stages. The first stage corresponds to the preparation of the lamellar lyotropic phase. The second stage is that of dispersion of this phase in the oil and the third stage corresponds to the emulsification of the oily dispersion in the aqueous continuous phase.

In this example, an aqueous solution of vitamin C, which will act as probe for the measurement of escape of example 3, is encapsulated.

The percentages are expressed by weight. This procedure is valid for amounts of the order of 10 to 100 g.

First Step:

Formulation 1

40% polyalkylene glycol of Elfacos ST9 type sold by Akzo Nobel    10% polysorbate 60

30% mineral oil sold as thick oil by Sigma

20% of a 20% aqueous vitamin C solution.

After having mixed the first three constituents at ambient temperature, the 20% vitamin C solution is added and then mixing is carried out with a spatula for to 15 minutes until a homogeneous mixture is obtained.

Second Step:

Formulation 2:

20% formulation 1

80% mineral oil

The two constituents are dispersed at ambient temperature and then the mixture is kept stirred for 10 to 15 minutes with a magnetic bar.

Third stage:
- 20% formulation 2
- 80% 1% aqueous solution of polyalkylene glycol of Elfacos OW 100 type (Akzo Nobel)

As soon as formulation 2 has been added, the mixture is stirred very vigorously by hand for 10 minutes. It is also possible to use a magnetic stirrer rotating at high speed.

The preparation is brought to pH=6. The content of vitamin C in the final product is 0.2% (by mass).

An emulsion is obtained, observation of which with a microscope shows the presence, inside the oil droplets, of multilamellar vesicles. Their characterization by optical microscopy is carried out as in example 2.

Example 2

Visualization by Optical Microscopy

In this example, a product analogous to that obtained in example 1, but in which the vitamin C is replaced by a procyanidol oligomer (PCO, referenced 'Grape seed extract', obtained from Vinyals, Barcelona, Spain), is compared with a product obtained according to a double emulsion process described in the literature. The procedure is the same as in example 1 but with the following formulations.

2a —Complex Medium According to the Invention

Formulation A
- 40% polyalkylene glycol of Elfacos ST9 type sold by Akzo Nobel
- 10% polysorbate 60
- 20% mineral oil
- 30% of a 10% aqueous PCO solution Formulation B
- 20% formulation A
- 80% mineral oil Formulation C
- 20% formulation B
- 80% 1% aqueous solution of polyalkylene glycol of Elfacos OW 100 type (Akzo Nobel)

2b —Double Emulsion (Comparative)

The double emulsion which is used for the comparison is obtained from the following formulation:

The percentages are expressed by mass.

A. A dispersion of Lipophilic Surfactant in the Oil is Prepared Beforehand
- 1% polyalkylene glycol of Elfacos ST9 type sold by Akzo Nobel
- 99% mineral oil B. A Water-in-Oil Emulsion is Prepared from the Mixture A
- 20% of 10% aqueous PCO solution
- 80% of the mixture prepared in A Mixing is carried out at ambient temperature by addition, with magnetic stirring, of the water to the oil.

C. The Water-in-Oil Emulsion B is Emulsified in an Aqueous Continuous Medium
- 20% of the mixture obtained in B
- 80% 1% aqueous solution of polyalkylene glycol of Elfacos OW 100 type (Akzo Nobel)

The mixture is obtained by stirring vigorously by hand. An off white emulsion is obtained.

2c—Characterization

The characterization method is polarized light optical microscopy, which makes it possible to demonstrate the birefringence of a structure related to its anisotropic nature and, in the case of the invention, to the liquid crystal nature of the lamellar structure of the vesicles.

On referring to FIGS. 1 to 4, the difference in appearance of the negatives is easily observed.

Figure 1:
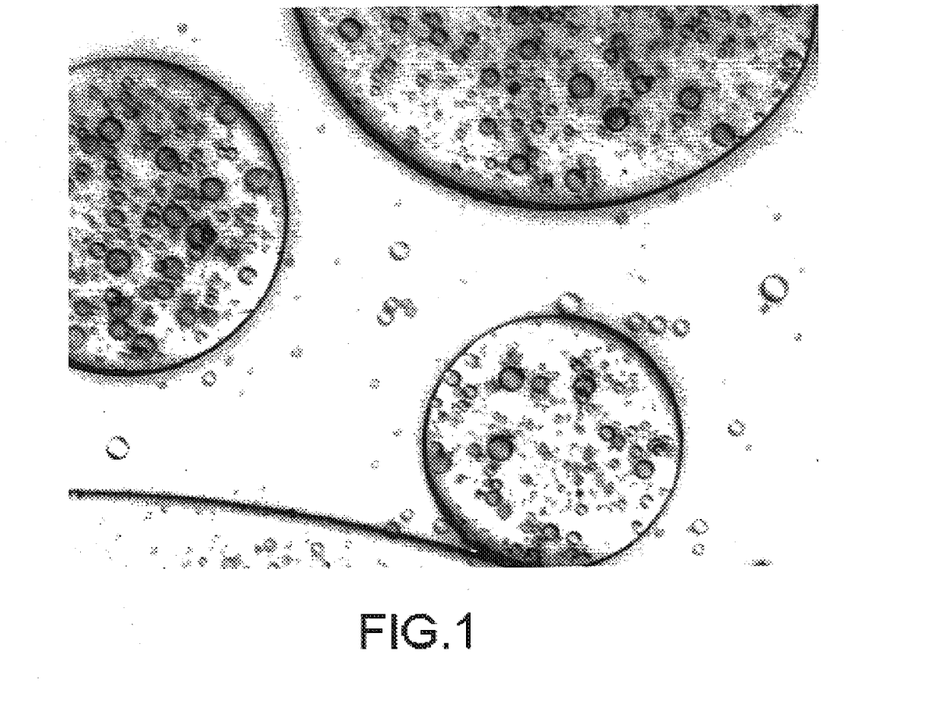
FIG. 1 represents a negative obtained in direct-light optical microscopy in the case of a conventional double emulsion.
Figure 2:
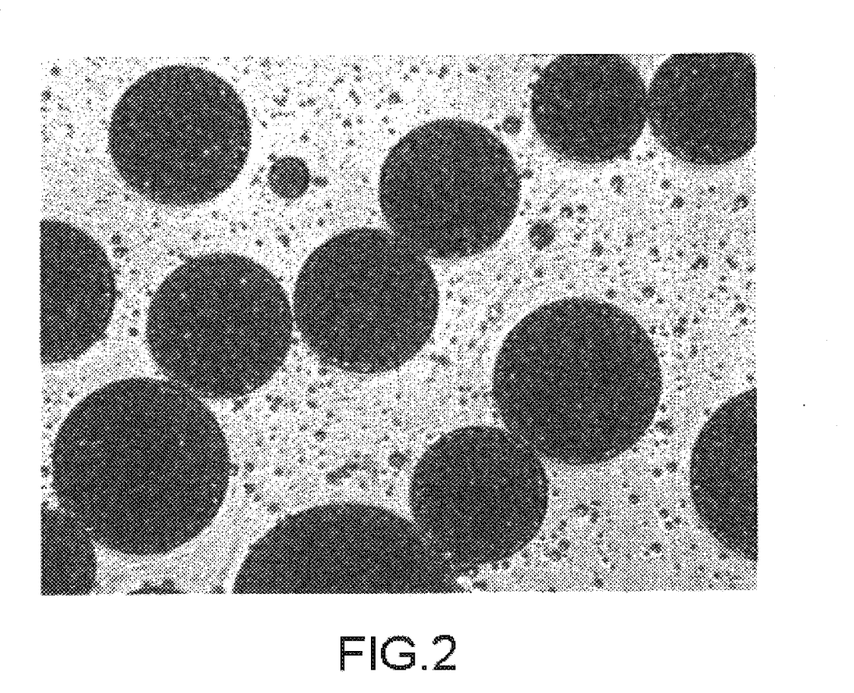
FIG. 2 represents the negative obtained in direct light in the case of the complex medium according to the invention described in example 2.
Figure 3:
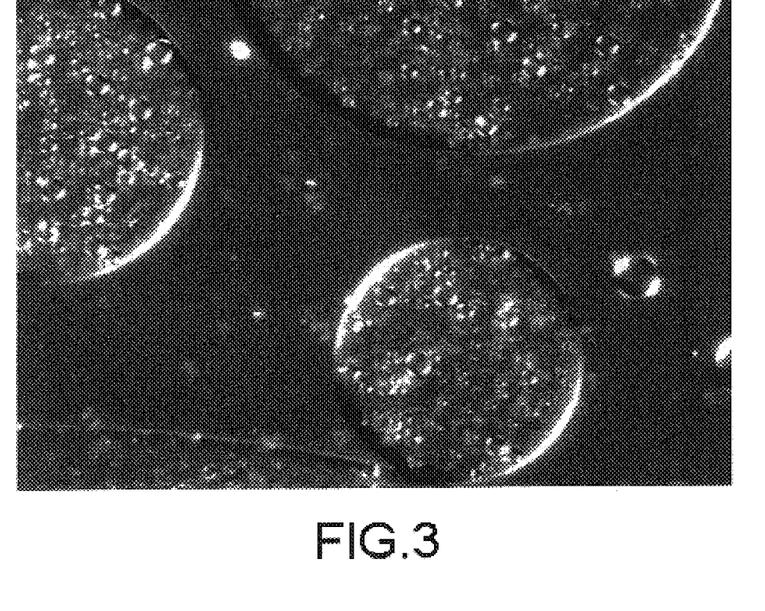
FIG. 3 represents the negative obtained in polarized light in the case of a conventional double emulsion.
Figure 4:
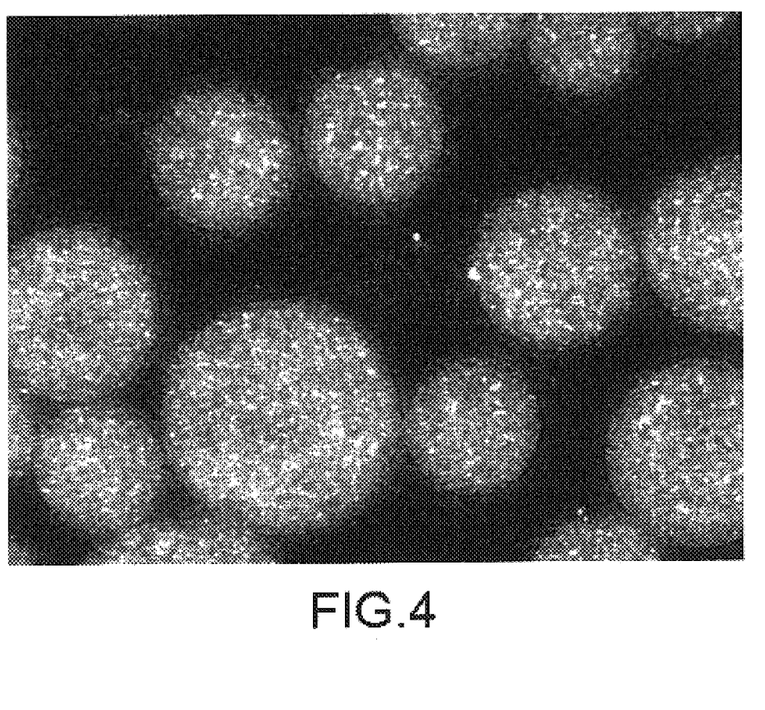

FIGS. 1 and 2 show that, in direct light, the multiple emulsion droplets are clear (transparent) (see FIG. 1), whereas the droplets of the complex dispersion according to the invention are opaque (see FIG. 2).

In polarized light, the multiple emulsion (FIG. 3) does not show birefringence (only a slight edge effect, conventional for the water/oil interface, is visible), whereas the complex dispersion of multilamellar vesicles (FIG. 4) shows strong birefringence inside the oily droplets. This birefringence shows that the vesicles have retained their anisotropic lamellar structure after dispersion in the oil. Furthermore, it should be noted that no birefringence is observed in the aqueous continuous medium, which indicates that the vesicles are all inside the oily droplets.

Example 3

Measurement of the Kinetics of Escape of Vitamin C

The measurement of kinetics of escape consists in quantitatively determining the vitamin C in the aqueous continuous medium of the complex dispersion prepared in ¢ example 1. To do this, first of all the aqueous and oily media of the external emulsion are separated and then the vitamin C is quantitatively determined by a chemical quantitative determination. For confirmation, the structure of a sample of the system is broken down, by addition of a detergent, in order to quantitatively determine all the vitamin C (final point).

a) Separation

The complex dispersion of example 1 is centrifuged at ambient temperature twice at 10,000 g. The supernatant, composed of the oily part, is separated and the low aqueous fraction is used for the quantitative determination.

b) Quantitative Determination

The quantitative determination of the vitamin C is carried out by quantitative determination with iodine, according to a conventional method. 30 g of water and 20 g of acetone are added to 20 g of aqueous solution. 4 drops of starch are added for the visualization of the end point. Quantitative determination is carried out by dropwise addition of a standard iodine solution.

c) Final Point

For the determination of the total amount of vitamin C present in the sample, the complex dispersion is broken down by addition of sodium lauryl sulfate (SDS). 3 g of SDS are added to a 30 g test sample. After stirring, a homogeneous solution is obtained, on which solution the quantitative determination with iodine is carried out.

d) Result

Figure 5:
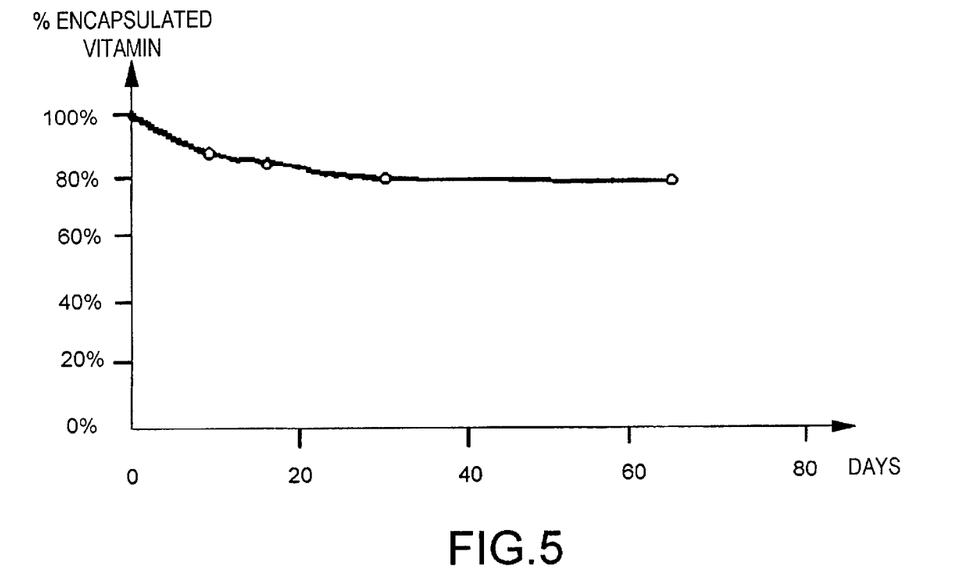

The curve represented in FIG. 5 gives the escape of the vitamin C over a period of 2 months. It is observed that it remains very low, less than 20%, and clearly stabilizes before this time. It may thus be concluded that the complex dispersion of the invention is an effective means for encapsulating an active principle and isolating it from the external medium.

Example 4

Comparison of the Stability Between Complex Dispersion and Double Emulsion

In order to compare the complex dispersion according to the invention with a double emulsion obtained by a conventional method, a double emulsion is prepared using the same surfactants as those participating in the formulation of the complex dispersion. Amaranth, a dye, is encapsulated in each case and acts as probe for monitoring the kinetics of escape of each of the formulations.

Complex Dispersion, Formulation A:

The complex dispersion is prepared according to the procedure given in example 1, the aqueous vitamin C solution being replaced by a $10^{-2}$ M aqueous amaranth solution.

Double Emulsion, Formulation B:

The double emulsion is prepared according to a conventional method from a first water-in-oil emulsion, itself emulsified in water. The surfactants employed are the same as those used for formulation A.

The first $W_1/O$ emulsion is prepared in the following way:

A $10^{-2}$ M amaranth solution is emulsified at 60% in mineral oil comprising 1% of a mixture of Elfacos ST9/ Polysorbate 60 (4/1) surfactants using powerful stirring.

This $W_1/O$ emulsion is subsequently emulsified in an aqueous phase comprising 1% of Elfacos OW 100.

The encapsulation yield of the amaranth for this formulation B is compared with that of the complex dispersion, formulation A, over time at 22° C. To do this, the formulation is separated by centrifuging, so as to isolate the external medium. A measurement of optical density by spectrometry with respect to this external medium makes it possible to determine the concentration of amaranth which has escaped. The result appears in FIG. 6.

Figure 6:
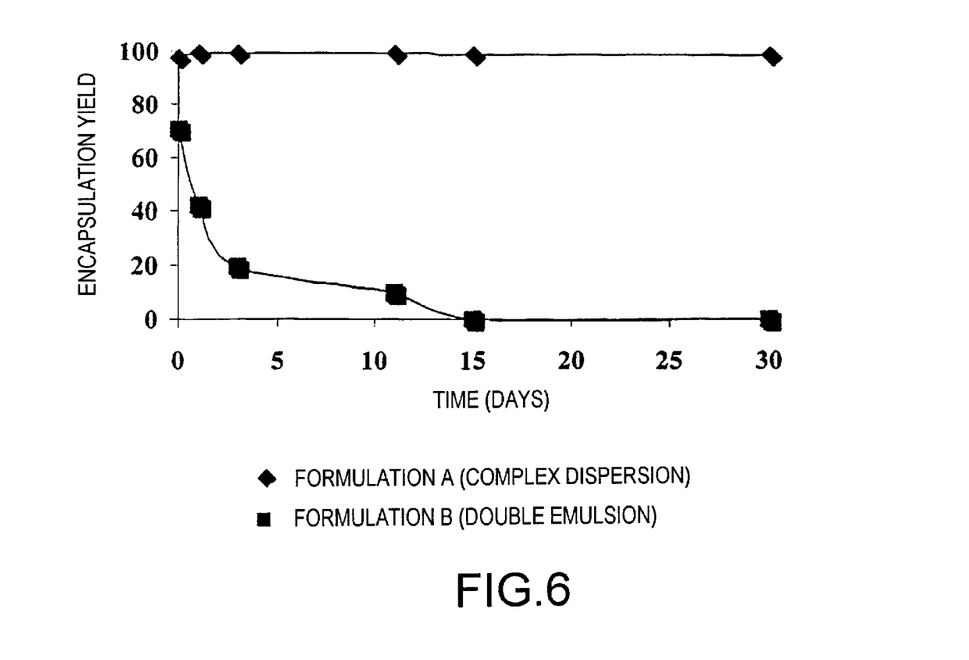

It is observed that, whereas all the dye has escaped in 15 days in the case of the double emulsion, all the dye is still encapsulated in the complex dispersion of the invention after 30 days. This demonstrates the fundamental difference in stability, related to the difference in nature, between a double emulsion and the complex dispersion according to the invention.

Example 5 pH differential

A composition according to the invention is prepared by encapsulating a pH indicator (Congo Red: purple/blue at pH3, red at pH5) inside the multilamellar vesicles.

Formulation of the multilamellar vesicles:

40% polyalkylene glycol of Elfacos ST9 type sold by Akzo Nobel

10% Polysorbate 60

30% Paraffin oil

20% Aqueous solution of colored indicator, the pH of which is adjusted with sodium hydroxide.

Two samples of vesicles are prepared, either with a solution of colored indicator at pH3, the vesicles are blue or with a solution of colored indicator at pH5.9, the vesicles are red.

Each sample is then dispersed at 20% in mineral oil, the dispersions retain the coloring and thus the pH of the vesicles.

Several complex dispersions are prepared from the preceding oily dispersions by dispersing 20% of oily dispersions in a 1% aqueous solution of polyalkylene glycol of Elfacos OW 100 type.

The demonstration of the leaktightness of the systems with respect to the colored indicator in its two pH forms is carried out with the following complex dispersions:

Oily dispersion of vesicles at pH 3 (blue) in a solution of Elfacos OW100 at pH 3

Oily dispersion of vesicles at pH 5.9 (red) in a solution of Elfacos OW100 at pH 6.5.

Aqueous solutions of Elfacos OW100 with 1% of colored indicator are prepared at pH 3.3 and 6.5 in order to confirm that the concentration of colored indicator encapsulated in the vesicles is sufficient to render visible the coloring of the external medium in the event of escape.

For the two systems prepared at pH 3 and 6.5, escape of the colored indicator from the vesicles toward the external aqueous medium is not observed, the external aqueous medium remaining colorless.

This point being confirmed, complex dispersions with differences in pH between the aqueous medium encapsulated in the vesicles and the external aqueous medium are prepared:

Oily dispersion of multilamellar vesicles with an onion structure at pH 3 (blue) in a solution of Elfacos OW100 at pH 6.5

Oily dispersion of multilamellar vesicles with an onion structure at pH 5.9 (red) in a solution of Elfacos OW100 at pH 3.3.

In the two complex dispersions, the vesicles retain their initial coloring, related to the preparation pH, and the external medium remains colorless. These preparations thus exhibit a discrepancy in pH between two compartments of the systems, thus making it possible to retain the acidity of an active principle while formulating it in a preparation at a higher pH and vice versa.

Example 6

Stability of the pH Differential

In this example, a small molecule, salicylic acid, which is insoluble in water, is encapsulated at a low pH (3.5), whereas the pH of the external medium is set at various values in the region of neutrality compatible with a cosmetic use (5 and 7).

Formulation of the Multilamellar Vesicles:

A formulation A of pure multilamellar vesicles is prepared according to the following composition:

37% polyalkylene glycol of Elfacos ST9 type sold by Akzo Nobel

9% Polysorbate 60

19% Mineral oil

10% Salicylic acid

25% Glycerol

The polyalkylene glycol (Elfacos ST9), the polysorbate 60, the mineral oil and the salicylic acid are mixed using a mechanical stirrer while heating at 80° C. until the salicylic acid has completely dissolved. The glycerol is subsequently added and stirring is continued until the mixture has returned to ambient temperature. A pure phase of multilamellar vesicles, which are dispersible in the oil, is thus obtained.

Dispersion in the Oil:

The preparation of concentrated multilamellar vesicles A thus obtained is dispersed in the mineral oil in the following proportions by mechanical stirring at ambient temperature:

65% Formulation A

35% Mineral oil

Formation of the Complex Dispersion:

The oily dispersion is then emulsified in an aqueous medium.

The aqueous medium is composed of a dispersion in water of 1% of polyalkylene glycol of Elfacos OW100 type and of 6% of Sepigel 305 (mixture of polyacrylamide, of $C_{13-14}$ isoparaffin and of laureth-4 sold by Seppic, Paris). The proportions of the two media are:

32% Oily dispersion

68% Aqueous solution

The emulsification is obtained by slow addition of the oily dispersion to the aqueous solution with mechanical stirring at ambient temperature.

The complex dispersion thus prepared has a concentration of salicylic acid of 2% and the pH is 3.5. It has the appearance and the texture of a cosmetic cream.

From this formulation, two preparations are prepared by adjusting the pH with triethanolamine to 5 and 7.

The pH stability of the three complex dispersions is monitored at ambient temperature. The result is given on the graph represented in FIG. 7, where the pH of each of the preparations is plotted as a function of the time.

Figure 7:
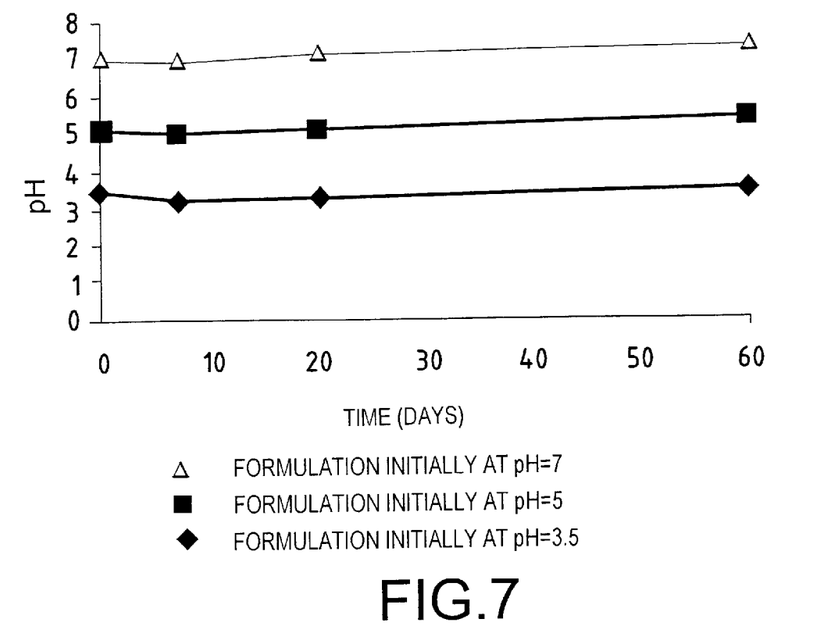

It is observed that, whatever the initial pH, no variation in pH appears in the cream over time. This means that, during the period observed, no escape of salicylic acid was found. The oil surrounding the multilamellar vesicles acts in this case as a barrier, preventing any diffusion between the internal medium, where the salicylic acid is found, and the external medium, where the pH was adjusted.

Example 7

Preparation of a Cosmetic Emulsion

A description is given in this example of the preparation according to the process of the invention of a cosmetic emulsion comprising, in the form of a complex dispersion, multilamellar vesicles encapsulating a procyanidol oligomer (PCO). This compound is a powerful but particularly unstable agent for combating free radicals which acquires a brown coloring under the effect of oxidation.

The percentages are by mass.

Step 1

This step is the stage of preparation of the multi-lamellar vesicles encapsulating the PCO.

40% Polyalkylene glycol of Elfacos ST9 type sold by Akzo Nobel

10% Polysorbate 60

20% Mineral oil

30% Aqueous solution comprising 10% of PCO.

After having mixed the Elfacos, the polysorbate and the mineral oil, the 10% PCO solution is added and then mixing is carried out with a spatula for 10 to 15 minutes until a homogeneous mixture is obtained.

A thick cream is obtained, which cream is a concentrated phase of multilamellar vesicles comprising 3% PCO.

Step 2

The formulation obtained in step 1, composed of a concentrated phase of multilamellar vesicles, is dispersed in a mineral oil.

20% Formulation 1

80% Mineral oil.

The dispersion is prepared simply at ambient temperature by slow incorporation of the mineral oil over the cream with manual stirring. The dispersion is subsequently mixed for 10 to 15 minutes with a magnetic bar and a magnetic stirrer.

Step 3

The oily dispersion of vesicles obtained in step 2 is emulsified in an aqueous medium. In order to obtain the desired texture and the desired stability, use is made of a gelling agent for the aqueous continuous phase.

A 1% dispersion of polyalkylene glycol of Elfacos OW 100 type comprising 1% of Sepigel 305 (mixture of polyacrylamide, of $C_{13-14}$ isoparaffin and of laureth-4 sold by Seppic) is prepared. This dispersion is obtained by incorporating the Sepigel in the surfactant dispersion with strong mechanical stirring.

Formulation

20% Formulation obtained in step 2

80% 1% dispersion of polyalkylene glycol of Elfacos OW 100 type comprising 1% of Sepigel The formulation obtained in step 2 is added to the dispersion of surfactants and of polymer with mechanical stirring.

A white cream is obtained which has a smooth feel, which is stable for several months at ambient temperature and which shows no tendency toward separating by settling or toward creaming.

Figure 8:
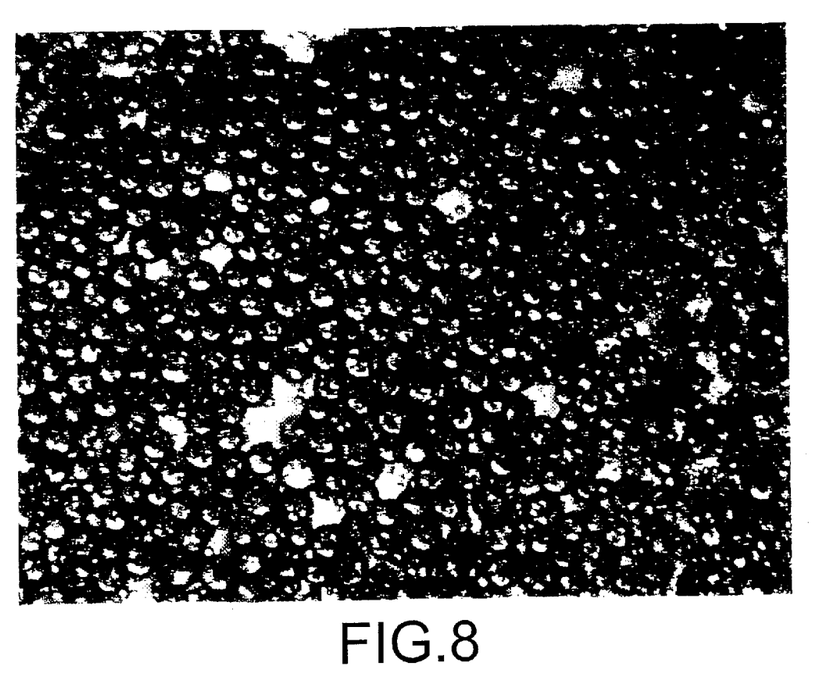
FIG. 8 is a negative obtained in polarized-light optical microscopy in the case of the cosmetic emulsion described in example 7 with a 20× objective and a 10× eyepiece.

As is apparent in FIG. 8, observation by polarized-light optical microscopy makes it possible to demonstrate the presence of the multilamellar vesicles inside the oil droplets.

Example 8

Preparation of Microspheres of Resorbable Polymer

In this example, the invention is used to prepare microspheres of a biodegradable polymer, poly-DL-lactide (Pla) with a mass of 43 000 g/mol distributed by Phusys.

Formulation:

A concentrated phase of multilamellar vesicles is prepared by mixing the following constituents at ambient temperature:

40% Soybean lecithin

10% Sorbitan oleate

50% Water.

This concentrated phase is quickly dispersed in a 10% (by mass) solution of polymer in dichloromethane. This dispersion is prepared in approximately 1 minute, so as to prevent decomposition of the vesicles. The ratio of the mass of polymer in solution to the dispersed mass of vesicles is 2.

This organic dispersion of vesicles is then emulsified at 3% in an aqueous solution comprising 1% by mass of poly(vinyl alcohol) with a mass of 30 000–70 000 distributed by Sigma. The solution is stirred with a magnetic bar while carrying out the addition. This stirring is continued for 2 to 3 hours without stopping the flask, so as to evaporate the organic solvent.

Once evaporation is complete, spherical objects can be observed by optical microscopy which are not destroyed by the addition of detergents, such as Triton X100 (Sigma), or by addition of a solution comprising 10% of deoxycholate salt (main constituent of bile salts). These detergents are known to dissolve lecithin-based structures. The resistance to these detergents of the objects obtained in this example shows that the external composition of these vesicles is not the phospholipid.

Observation by Electron Microscopy:

Transmission electron microscopy negatives show the presence, inside the polymer microspheres, of a dark mass, the composition of which cannot be determined, whereas empty microspheres of the same polymer (prepared from an emulsion not comprising the multilamellar vesicles) show a core which is transparent by the same observation technique.

Encapsulation of a Dye:

A hydrophilic dye (methylene blue) can be incorporated in the initial lamellar phase before the stage of dispersion in the organic solution. The microspheres of polymer Pla are subsequently prepared according to the same procedure as above. Polymer microspheres are then obtained which incorporate multilamellar vesicles which encapsulate the dye.

The encapsulation yield is measured by quantitatively determining, by UV/visible spectrophotometry, the dye in the supernatant after separation of the microspheres by centrifuging. An encapsulation yield of 85% is found, which shows that the vesicles have not been decomposed during the stage of formation of the polymer microspheres.

Example 9

Encapsulation of an Antigen for Amplifying the Immune Response

The invention can be used to encapsulate an antigen in order to vectorize it and thus to amplify the immune response. It is shown here that the use of a complex dispersion formed from multilamellar vesicles encapsulating the antigen makes it possible to greatly amplify the immune response.

The model chosen is human serum albumin (HSA) injected subcutaneously in mice. The immune response is measured by the ELISA test, which quantitatively determines the total anti-HSA antibodies in the serum of the mice.
Formulation The multilamellar vesicles are prepared from:

| | |
|---|---|
| Potassium oleate | 5% |
| Cholesterol | 5% |
| Cholesterol sulfate | 2.5% |
| Lauryl alcohol ethoxylated with 4 ethylene oxide (laureth-4) | 2% |
| PBS 1× | 20% |
| HSA as a 20 mg/ml solution in PBS 1× | 20% |
| 90% Phosphatidylcholine (PC90 Natterman) | 45.5% |

The first five constituents are mixed and then incubated for 1 h at 90° C. until the cholesterol and cholesterol sulfate crystals have completely disappeared. After cooling to ambient temperature, the HSA solution and then the phosphatidylcholine are slowly incorporated. The mixture is incubated for 2 hours at 37° C. and is then sheared manually for 5 minutes.

The concentrated paste obtained is separated into two batches before dispersion. It is titered at 4 mg/g of HSA.

One batch is dispersed at 5% by addition of an aqueous PBS buffer. The final concentration of HSA is 20 µg per 100 µl (0.02% by mass).

The other batch is dispersed in a mineral oil in a proportion of 200 mg of paste per 0.8 ml of oil. The dispersion is obtained by slowly adding the mineral oil to the paste at ambient temperature with manual stirring.

This oily dispersion is emulsified as described in example 1 by addition of the oily dispersion to a 1% aqueous solution of polyalkylene glycol of Elfacos OW 100 type (Akzo Nobel) in a proportion of 0.25 ml of oil per 0.75 ml of aqueous solution. The mixture is homogenized by vigorous manual stirring. The final HSA titer is 20 µg per 100 µl of dispersion.
Protocol The preparations are injected subcutaneously into groups of 4 female BALB/c mice at the rate of one injection at t=0 and then one injection at t=10 days. A control group is not injected, one group receives the aqueous dispersion and the other group receives the complex dispersion. The mice are sacrificed at t=23 days, the blood is withdrawn into heparinized tubes and the serum is isolated by centrifuging.

Quantitative determination of the total immunoglobulins is carried out by the ELISA test on these sera according to a conventional protocol using rabbit immunoglobulins against mouse immunoglobulins labeled with peroxidase. The fixed immunoglobulins are revealed by the addition of the enzyme substrate, which gives a colored product absorbing at 490 nm. For each serum, the reaction is carried out with respect to a series of dilutions from 1/25 to $1/(25 \times 2^{11})$.
Results The measurement is carried out by recording the optical density (OD) at 490 nm as a function of the dilution of the serum. The positivity threshold is defined as the mean value of the OD obtained for the first dilution (1/25) with the sera of the four non-injected control mice, increased by t times the standard deviation for this mean value, or t is the value defined in the Student method (cf. European Pharmacopoeia, statistical methods).

The results are expressed as mean titer, defined as the dilution factor for the serum for which the mean OD for the four mice of the group is greater than the positivity threshold. The following titers are obtained:

| | Mean titre of total IgGs |
|---|---|
| HSA in PBS | 0 |
| Aqueous dispersion | 2870 |
| Complex dispersion | 17900 |

A significant response is thus observed as an aqueous dispersion but a very markedly greater response is observed by injection of the formulation as a complex dispersion according to the invention.

What is claimed is:

1. A complex medium composed of a first medium in the form of droplets of a size between 1 and 50 µm having dispersed therein a lyotropic phase formed from bilayers of surfactants, said droplets being in emulsion within a second medium, which is a continuous phase that is immiscible with the first medium.

2. The complex medium as claimed claim 1, wherein said emulsion comprises from 1 to 90% by weight of the first medium.

3. The complex medium as claimed in claim 1, wherein said droplets comprise from 1 to 90% by weight of the lyotropic phase.

4. The complex medium as claimed in claim 1, wherein said first medium is a hydrophobic medium and said continuous phase is an aqueous medium.

5. The complex medium as claimed in claim 1, wherein said bilayers are in the form of multilamellar vesicles with an onion structure, of substantially spherical shape comprising a uniform sequence of concentric bilayers, from a center to a periphery of said vesicles.

6. The complex medium as claimed in claim 1, wherein said vesicles have dimensions of between 0.1 and 20 µm.

7. The complex medium as claimed in claim 1, which is a dispersion of multilamellar vesicles having an onion structure, of substantially spherical shape comprising a uniform sequence of concentric bilayers, from a center to a periphery of said vesicles, within droplets of a hydrophobic medium, said droplets being emulsified within an aqueous medium.

8. The complex medium as claimed in claim 1, wherein the continuous phase includes at least one surfactant enabling emulsification of the dispersion comprising the lyotropic phase comprising bilayers in the first medium.

9. The complex medium as claimed in claim 8, wherein the continuous phase comprises at least one surfactant having a molecular weight greater than 1,000 Da.

10. The complex medium as claimed in claim 8, wherein said surfactant is a surfactant of polymer type selected from the group consisting of poloxamers, copolymers of polyalkylene glycol and alkyl glycol, polyglycerides, ethers of fatty alcohols and glycerol polymers, esters of fatty acids and polyethylene glycol, and ethers of fatty alcohols and polyethylene glycol.

11. The complex medium as claimed in claim 1, wherein said first medium is a hydrophobic medium comprising a substance capable of solidifying, thickening, polymerizing or precipitating, or a solution of said substance in a water-immiscible solvent capable of evaporating.

12. The complex medium as claimed in claim 1, further comprising at least one active principle.

13. The complex medium as claimed in claim 1, further comprising at least one chemical or biological active principle incorporated within the lyotropic phase comprising bilayers.

14. A process for the preparation of a complex medium comprising a first medium in the form of droplets having dispersed therein a lyotropic phase formed from bilayers of surfactants, said droplets being in emulsion within a second medium, which is a continuous phase that is immiscible with the first medium, comprising the steps of:

preparing a condensed lyotropic phase formed from bilayers of surfactants;

dispersing said phase in a first medium to obtain a dispersion;

emulsifying the dispersion in a second medium, immiscible with the first medium, by means of a surfactant; and optionally incorporating at least one active principle in at least one of the lyotropic phase comprising the bilayers, the first medium and the second medium.

15. The process as claimed in claim 14, wherein said lyotropic phase comprises multilamellar vesicles with an onion structure, of substantially spherical shape comprising a uniform sequence of concentric bilayers, from a center to a periphery of said vesicles.

16. A process for preparing polymer microspheres incorporating an active principle, comprising the steps of:

preparing a lyotropic phase including said active principle;

dispersing the phase in a hydrophobic medium in which a monomer or a polymer capable of being crosslinked is dissolved, or in a medium comprising a hydrophobic solvent in which a polymer is dissolved, to form a dispersion;

preparing an emulsion in the form of droplets of said dispersion in a medium which is immiscible with the hydrophobic medium; and converting said droplets into solid grains, by polymerization of the monomer or crosslinking of the polymer or precipitation of the polymer, respectively.

17. Polymer microspheres obtained by the process as claimed in claim 16.

18. A process for controlling the release of an active principle or protecting the active principle from decomposition, comprising incorporating said active principle in a condensed lyotropic phase formed from bilayers of surfactants, dispersing the phase comprising the active principle in a first medium and emulsifying said first medium in a second medium which is immiscible with said first medium.

19. A complex medium composed of a first medium in the form of droplets having dispersed therein a lyotropic phase formed from bilayers of surfactants, said droplets being in emulsion within a second medium, which is a continuous phase that is immiscible with the first medium, said bilayers being in the form of multilamellar vesicles with an onion structure, of substantially spherical shape comprising a uniform sequence of concentric bilayers, from a center to a periphery of said vesicles.

20. The complex medium as claimed in claim 19, wherein the droplets have a size between 1 and 100 $\mu$m.

21. The complex medium as claimed in claim 20, wherein the droplets have a size between 1 and 50 $\mu$m.

22. The complex medium as claimed claim 19, wherein said emulsion comprises from 1 to 90% by weight of the first medium.

23. The complex medium as claimed in claim 19, wherein said droplets comprise from 1 to 90% by weight of the lyotropic phase.

24. The complex medium as claimed in claim 19, wherein said first medium is a hydrophobic medium and said continuous phase is an aqueous medium.

25. The complex medium as claimed in claim 19, wherein said vesicles have dimensions of between 0.1 and 20 $\mu$m.

26. The complex medium as claimed in claim 19, wherein the continuous phase includes at least one surfactant enabling emulsification of the dispersion comprising the lyotropic phase comprising bilayers in the first medium.

27. The complex medium as claimed in claim 26, wherein the continuous phase comprises at least one surfactant having a molecular weight greater than 1,000 Da.

28. The complex medium as claimed in claim 26, wherein said surfactant is a surfactant of polymer type selected from the group consisting of poloxamers, copolymers of polyalkylene glycol and alkyl glycol, polyglycerides, ethers of fatty alcohols and glycerol polymers, esters of fatty acids and polyethylene glycol, and ethers of fatty alcohols and polyethylene glycol.

29. The complex medium as claimed in claim 19, wherein said first medium is a hydrophobic medium comprising a substance capable of solidifying, thickening, polymerizing or precipitating, or a solution of said substance in a water-immiscible solvent capable of evaporating.

30. The complex medium as claimed in claim 19, further comprising at least one active principle.

31. The complex medium as claimed in claim 29, wherein the active principle comprises at least one chemical or biological active principle incorporated within the lyotropic phase.

32. A complex medium composed of a first, hydrophobic medium in the form of droplets having dispersed therein a lyotropic phase formed from bilayers of surfactants, said droplets being in emulsion within a second, aqueous medium, which is a continuous phase that is immiscible with the first medium.

33. The complex medium as claimed in claim 32, wherein the droplets have a size between 1 and 100 $\mu$m.

34. The complex medium as claimed in claim 33, wherein the droplets have a size between 1 and 50 $\mu$m.

35. The complex medium as claimed claim 32, wherein said emulsion comprises from 1 to 90% by weight of the first medium.

36. The complex medium as claimed in claim 32, wherein said droplets comprise from 1 to 90% by weight of the lyotropic phase.

37. The complex medium as claimed in claim 32, wherein said vesicles have dimensions of between 0.1 and 20 $\mu$m.

38. The complex medium as claimed in claim 32, wherein the continuous phase includes at least one surfactant enabling emulsification of the dispersion comprising the lyotropic phase comprising bilayers in the first medium.

39. The complex medium as claimed in claim 38, wherein the continuous phase comprises at least one surfactant having a molecular weight greater than 1,000 Da.

40. The complex medium as claimed in claim 38, wherein said surfactant is a surfactant of polymer type selected from the group consisting of poloxamers, copolymers of polyalkylene glycol and alkyl glycol, polyglycerides, ethers of fatty alcohols and glycerol polymers, esters of fatty acids and polyethylene glycol, and ethers of fatty alcohols and polyethylene glycol.

41. The complex medium as claimed in claim 32, wherein said first medium is a hydrophobic medium comprising a substance capable of solidifying, thickening, polymerizing or precipitating, or a solution of said substance in a water-immiscible solvent capable of evaporating.

42. The complex medium as claimed in claim 32, further comprising at least one active principle.

43. The complex medium as claimed in claim 32, wherein the active principle comprises at least one chemical or biological active principle incorporated within the lyotropic phase.

44. The complex medium as claimed in claim 32, wherein said bilayers are in the form of multilamellar vesicles with an onion structure, of substantially spherical shape comprising a uniform sequence of concentric bilayers, from a center to a periphery of said vesicles.

45. A process for the preparation of a complex medium comprising a first medium in the form of droplets having dispersed therein a lyotropic phase comprising multilamellar vesicles with an onion structure, of substantially spherical shape comprising a uniform sequence of concentric bilayers, from a center to a periphery of said vesicles, said droplets being in emulsion within a second medium, which is a continuous phase that is immiscible with the first medium, comprising the steps of:

preparing a condensed lyotropic phase formed from multilamellar vesicles with said onion structure, of substantially spherical shape comprising a uniform sequence of concentric bilayers, from a center to a periphery of said vesicles;

dispersing said phase in a first medium to obtain a dispersion;

emulsifying the dispersion in a second medium, immiscible with the first medium, by means of a surfactant; and optionally incorporating at least one active principle in at least one of the lyotropic phase comprising the bilayers, the first medium and the second medium.

46. The process as claimed in claim 45, wherein said vesicles are prepared by the converting a lamellar liquid crystal phase containing at least one surfactant by shearing.

47. A process for preparing polymer microspheres incorporating an active principle, comprising the steps of:

preparing a lyotropic phase comprising multilamellar vesicles with an onion structure, of substantially spherical shape comprising a uniform sequence of concentric bilayers, from a center to a periphery of said vesicles, said vesicles including said active principle;

dispersing the phase in a hydrophobic medium in which a monomer or a polymer capable of being crosslinked is dissolved, or in a medium comprising a hydrophobic solvent in which a polymer is dissolved, to form a dispersion;

preparing an emulsion in the form of droplets of said dispersion in a medium which is immiscible with the hydrophobic medium; and converting said droplets into solid grains, by polymerization of the monomer or crosslinking of the polymer or precipitation of the polymer, respectively.

48. Polymer microspheres obtained by the process as claimed in claim 47.

49. A process for controlling the release of an active principle or protecting the active principle from decomposition, comprising incorporating said active principle in a condensed lyotropic phase comprising multilamellar vesicles with an onion structure, of substantially spherical shape comprising a uniform sequence of concentric bilayers, from a center to a periphery of said vesicles, dispersing the phase comprising the active principle in a first medium and emulsifying said first medium in a second medium which is immiscible with said first medium.

* * * * *